United States Patent
Chang et al.

(10) Patent No.: US 11,098,336 B2
(45) Date of Patent: Aug. 24, 2021

(54) BIOSYNTHESIS OF BIOORTHOGONAL AMINO ACIDS

(71) Applicant: The Regents of the University of California, Oakland, CA (US)

(72) Inventors: Michelle C. Y. Chang, Berkeley, CA (US); Jorge A. Marchand Benmaman, Berkeley, CA (US); Monica E. Neugebauer, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 172 days.

(21) Appl. No.: 16/600,502

(22) Filed: Oct. 13, 2019

(65) Prior Publication Data

US 2020/0048674 A1 Feb. 13, 2020

Related U.S. Application Data

(63) Continuation of application No. PCT/US2018/029229, filed on Apr. 24, 2018.

(60) Provisional application No. 62/489,441, filed on Apr. 24, 2017.

(51) Int. Cl.
*C12P 21/00* (2006.01)
*C12N 9/16* (2006.01)

(52) U.S. Cl.
CPC ............... *C12P 21/00* (2013.01); *C12N 9/16* (2013.01)

(58) Field of Classification Search
CPC .................................. C12P 21/00; C12N 9/16
See application file for complete search history.

(56) References Cited

PUBLICATIONS

Kim et al., Nature Communications, 11:1867, 1-7, 2020.*

* cited by examiner

*Primary Examiner* — Maryam Monshipouri
(74) *Attorney, Agent, or Firm* — Richard Aron Osman

(57) ABSTRACT

Recombinant enzymes BesA, BesB, BesC, BesD and/or BesE are used generate non-canonical amino acids comprising a useful functional group, such as an alkynlyl, alkenyl or halogen.

20 Claims, 4 Drawing Sheets

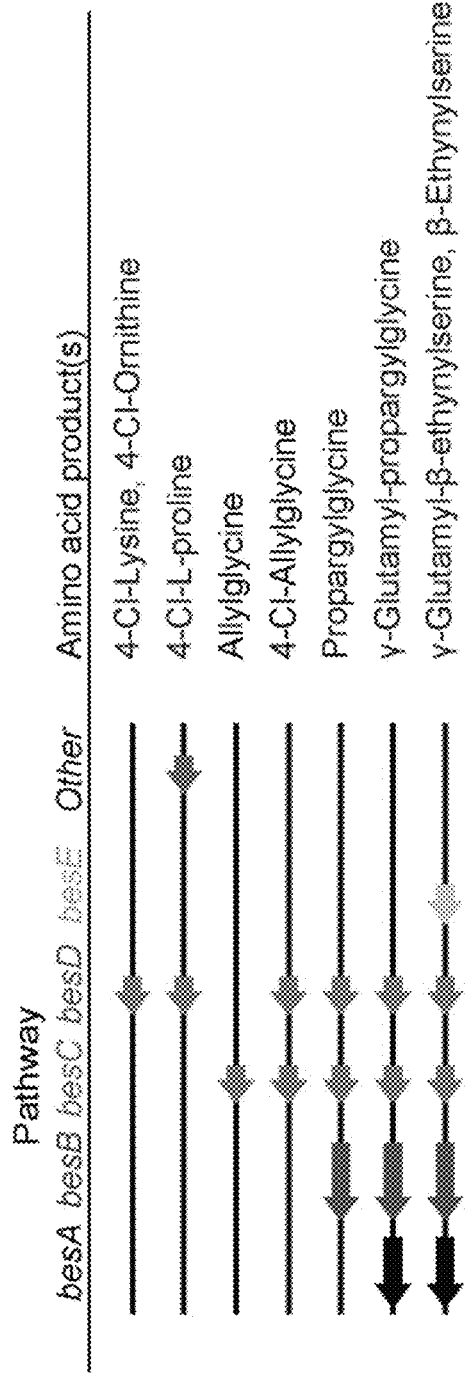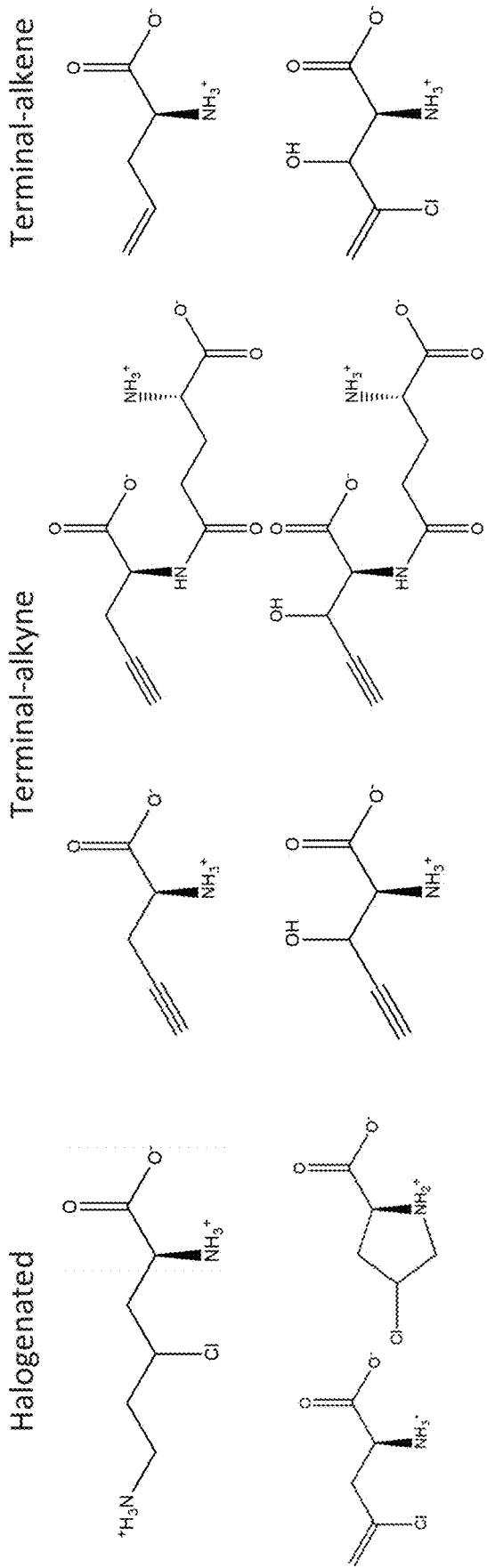
Fig. 1

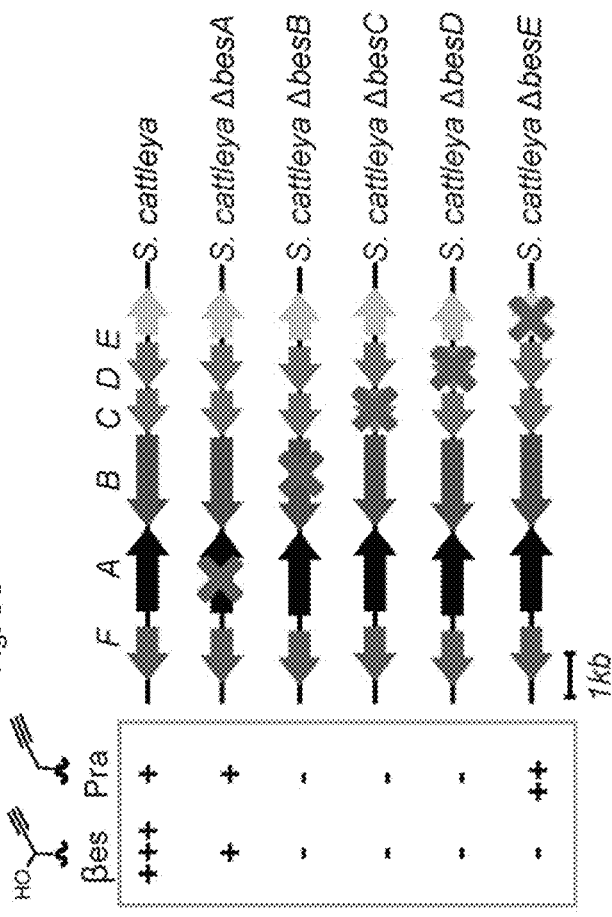

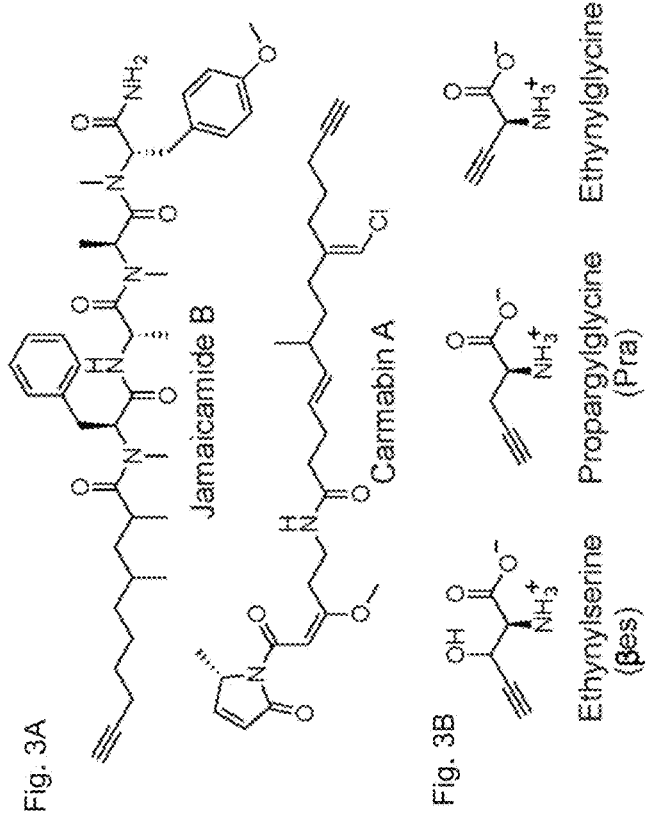

| Gene | a.a | Homologue | %ID/%S | Proposed function |
|---|---|---|---|---|
| besF | 297 | EamA family transporter [Streptomyces xylophagus] | 69/78 | Amino acid transporter |
| besA | 511 | Carboxylate-amine ligase [Cylindrospermopsis raciborskii] | 32/50 | Amino acid ligase |
| besB | 465 | Cystathionine beta-lyase [Opitutaceae bacterium TSB47] | 42/54 | Gamma-lyase |
| besC | 252 | Pyrroloquinoline-quinone synthase [Marinobacter pelagius] | 44/65 | Halogenase |
| besD | 268 | ArpA protein [Pseudomonas azotoformans] | 56/71 | Oxidase |
| besE | 257 | Proline hydroxylase [Streptomyces misionensis] | 54/66 | Hydroxylase |

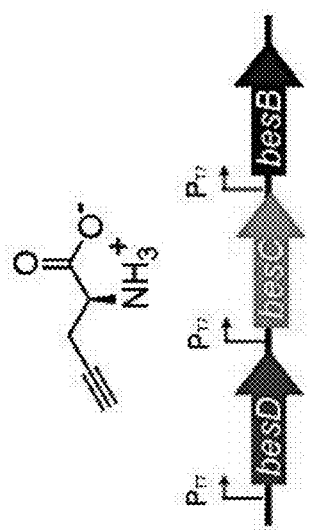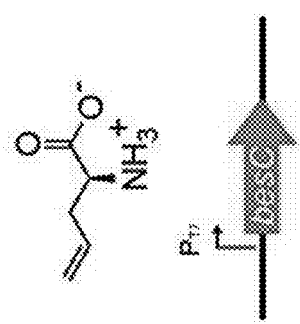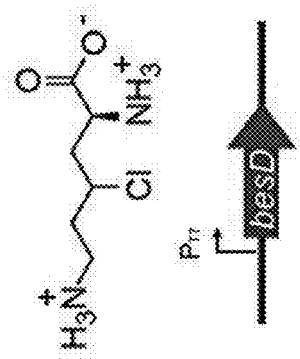
Fig. 4

BIOSYNTHESIS OF BIOORTHOGONAL AMINO ACIDS

This invention was made with government support under Grant Number OD008696 awarded by the National Institutes of Health. The government has certain rights in the invention.

INTRODUCTION

Living systems have been able to construct an enormous range of functions from a relatively limited set of functional groups, especially compared to the functional group and chemical reaction diversity that is available to synthetic chemists. As such, several bio-orthogonal reactions have been developed; taking advantage of the absence of certain functional groups inside the cell that can then be used as a specific chemical handle for a reacting partner when incorporated into a metabolite or macromolecule of interest. One of the most useful of these bio-orthogonal functional groups has been the terminal-alkyne, which can be used within the complex cellular milieu to react selectively with another bio-orthogonal group, the azide, to ligate the two reacting partners in a biocompatible copper-catalyzed azide alkyne cycloaddition (CuAAC or "Cu-Click") reaction.

Since its discovery, the CuAAC has found broad utility in a wide range of applications such as attachment of fluorescent probes, pull down and discovery of small molecule and protein binding partners, ligation to bioactive payloads (e.g. antibody-drug conjugates), or modifying macromolecular solubility and stability (e.g. PEGylation or tethering to solid supports). However, the application of this reaction to living systems has thus far been constrained to those that allow for alkyne and azide analogues that must ultimately be prepared by chemical synthesis and supplied exogenously.

SUMMARY OF THE INVENTION

Terminal alkynes, terminal alkenes, and organohalogens are some of the useful synthetic handles that have found broad utility in a wide range of applications such as attachment of fluorescent probes, pull down and discovery of small molecule and protein binding partners, ligation to bioactive payloads (e.g. antibody-drug conjugates), or modifying macromolecular solubility and stability (e.g. PEGylation or tethering to solid supports) [2,3,4,5,6,7]. However, introducing these functional groups into proteins in living systems has thus far been constrained to those that allow for alkynes, alkenes, and halogenated amino acid analogues that must ultimately be prepared by chemical synthesis and supplied exogenously [8].

Prior to our invention the terminal alkyne, terminal alkene, and halogenated amino acid must be fed exogenously to cells for incorporation into proteins, peptides, or natural products. The ability to genetically encode the biosynthesis of amino acids containing these functional groups enables new applications such as targeting to tissues in a living organism, while offering advantages in spatiotemporal control, reduced toxicity, and reduced background when compared to traditional feeding/injection [9, 10]. In addition, engineering a host that can produce these amino acids from glucose decreases the cost of industrial scale production of synthetically modifiable proteins [11]. In an aspect the invention leverages a natural pathway from BES biosynthesis (components of pathway summarized in Table 1) for the production of non-canonical amino acids with terminal-alkyne, terminal-alkene, and halogenated side chains in vivo or ex vivo that can have far reaching impact in applications such as reducing costs and improving activity of industrial enzymes, or making biological therapeutics, such as antibody-drug conjugates, newly accessible through fermentation.

Traditional methods for incorporating non-canonical amino acids into proteins, peptides, and non-ribosomal small molecules requires feeding of noncanonical amino acid building blocks to host organisms. In multicellular organisms, delivery of these amino acids to specific tissues is often difficult due to limitations in transport and stability of amino acids within the host. In many applications, a high concentration of non-canonical amino acids, which might be required for effective transport to the intracellular environment, can also be toxic to host organism. Additionally, amino acids that are used for incorporation need to be cost effective to synthesize which limits the amino acids that can be used for cost-sensitive applications.

Unlike traditional methods, the disclosed reactions and pathways allow for the de novo biosynthesis of a wide assortment of functionally useful non-canonical amino acids from any carbon source. Our methods: a) are more cost effective since these amino acids are produced from available carbon source; b) allow for spatial control of amino acids (tissue targeted delivery) through genetic engineering of desired tissue or cell line; c) lower costs for incorporating amino acids that are structurally useful but difficult to synthesize; d) allow for temporal control of amino acids through inducible expression of desired pathway; e) contain modular components that can be used for making an assortment of amino acids from few parts; and/or f) can lower toxicity associated feeding non-canonical amino acids to organisms since amino acids are produced within the cell.

Applications of reactions and pathways of the invention include:

Biosynthesis of antibodies with site specific terminal-alkyne, terminal-alkene, or halogenated amino acid residues in eukaryotes for producing antibody-drug conjugates from common carbon source.

Biosynthesis of proteins of interest such as glucose isomerase, with terminal-alkyne, terminal-alkene, or halogenated amino acid residues for chemical ligation onto solid surface from common carbon source.

Biosynthesis of amino acid-containing ribosomally or non-ribosomally synthesized therapeutics with halogenated, terminal-alkyne, or terminal-alkene side chains from common carbon source.

Cell-line specific labeling of proteome with terminal-alkyne, terminal-alkene, or halogenated amino acids in multicellular organisms for proteomics.

Engineering of an organism with an expanded genetic code that can produce amino acids with halogenated, terminal-alkyne, or terminal-alkene side chains from common carbon sources.

Chemo-enzymatic synthesis of terminal-alkyne, terminal-alkene, and halogen-containing small molecules in vitro.

The invention provides methods and compositions for synthesis of terminal alkyne, alkene, and halogenated amino acids in vitro and in vivo. The invention provides the first biosynthetic pathway for de novo synthesis of bioorthogonal amino acids. Applications include the production of value-added amino acids like 4-Cl-Lysine, and in vivo protein labeling, including antibody-drug conjugates, labeled proteins and immobilization of proteins. In embodiments the invention provides:

1. Biosynthesis of antibodies with site specific halogenated, terminal-alkyne, or terminal-alkene residues in eukaryotes for producing antibody-drug conjugates from common carbon source.

2. Biosynthesis of industrial enzymes, such as glucose isomerase, with halogenated, terminal-alkyne, or terminal-alkene residues for chemical ligation onto solid surface from common carbon source.

3. Biosynthesis of amino acid containing ribosomally or non-ribosomally-synthesized therapeutics with halogenated, terminal-alkyne, or terminal-alkene side chains from common carbon source.

4. Cell-line specific labeling of proteome with terminal-alkyne, terminal-alkene, or halogenated amino acids in multicellular organisms for proteomics.

5. Engineering of an organism with an expanded genetic code that can produce amino acids with halogenated, terminal-alkyne, or terminal-alkene side chains from common carbon sources.

6. Producing proteins/peptides for "Click-chemistry" applications, either Copper Catalyzed Azide Alkyne Cycloadditions (CuAAC) or Tetrazine Ligation (Reverse electron demand Diels-Alder)

7. Chemo-enzymatic synthesis of terminal-alkyne, terminal-alkene, and halogen-containing small molecules in vitro.

8. Making material (polymer) building blocks that contain terminal alkyne, terminal alkenes, or halogens using living organisms.

Other applications and indications will be apparent to those skilled in the art, including analogous indications and application of aldehyde tags, e.g. U.S. Pat. No. 7,985,783.

In aspects the invention provides methods of using enzymes BesA, BesB, BesC, BesD and BesE alone or in any combinations, to catalyze disclosed reactions, including fermentative production of a wide variety of non-canonical amino acids with useful functional groups; exemplary catalysis pathways are disclosed herein.

The disclosed specific examples are of course not limiting. BesB can be used alone to create terminal-alkyne amino acids in vivo or in vitro by supplying synthetic halo-alkene amino acids, e.g.:

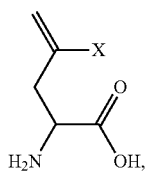

wherein X is halide (F, Cl, Br or I).

BesA can be used alone to make gamma-glutamyl dipeptides of propargylglycine in vitro or in vivo if synthetic propargylglycine is supplied. In addition other amino acids, particularly synthetic amino acids, can also be ligated by this enzyme to form dipeptides.

BesE alone can be used to generate hydroxylated amino acid dipeptides at the beta position, and aliphatic amino acids can also be used as substrates, e.g.:

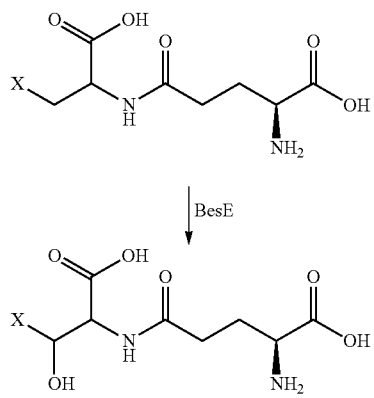

wherein X is C2-C4 alkyl, alkyl or alkynyl, such as CCH, CHCH$_2$ or CH$_2$CH$_3$.

BesA, BesB, BesC, BesD and BesE proteins are readily identified by those skilled in the art by function and sequence similarity. BesA, BesB, BesC, BesD, or BesE of different species (orthologs or homologs) catalyze the same reaction and have greater than 20, 40, 60 or 80% identity in amino acid sequence; for example, we easily identify such homologs of BesC and BesD from distant organisms that catalyzed the same reaction. These homologs are in the range of 40-50% identity in amino acid sequence, 50-60% in amino acid similarity.

Analogous homologs of BesD catalyze the same reactions that halogenate other amino acids or halogenate on different positions on lysine; analogous homologs of BesC catalyze reactions that lead to terminal desaturation of amino acids; and analogous homologs of BesB, BesA, or BesE catalyze the same disclosed reactions.

The substrates and reaction products are predetermined, and non-natural, i.e. not natural substrates and reaction products of the enzyme as they naturally exist in nature, but are rather xeno-, foreign substrates and reaction products which are not naturally associated with (reacted up or produced by) the enzyme.

The invention encompasses all combination of the particular embodiments recited herein, as if each combination had been laboriously recited.

SUMMARY REFERENCES

[1] E. M. Sletten and C. R. Bertozzi, "Bioorthogonal chemistry: fishing for selectivity in a sea of functionality," Angew. Chem. Int. Ed Engl., 48, no. 38, pp. 6974-6998, 2009.

[2] J. Liu, Y. Xu, D. Stoleru, and A. Salic, "Imaging protein synthesis in cells and tissues with an alkyne analog of puromycin," Proc. Natl. Acad. Sci., 109, no. 2, pp. 413-418, January 2012.

[3] M. P. VanBrunt et al., "Genetically Encoded Azide Containing Amino Acid in Mammalian Cells Enables Site-Specific Antibody—Drug Conjugates Using Click Cycloaddition Chemistry, Bioconjug. Chem., p. 150911072412002, 2015.

[4] M. Wu, H. Zhang, Z. Wang, S. Shen, X. C. Le, and X.-F. Li, "'One-pot' fabrication of clickable monoliths for enzyme reactors," Chem. Commun., 49, no. 14, pp. 1407-1409, January 2013.

[5] J. E. Moses and A. D. Moorhouse, "The growing applications of click chemistry," Chem. Soc. Rev., 36, no. 8, p. 1249, 2007.

[6] Y.-J. Lee, Y. Kurra, Y. Yang, J. Torres-Kolbus, A. Deiters, and W. R. Liu, "Genetically encoded unstrained olefins for live cell labeling with tetrazine dyes.," Chem. Commun. (Camb)., 50, no. 86, pp. 13085-8, 2014.

[7] U. Rieder and N. W. Luedtke, "Alkene-Tetrazine Ligation for Imaging Cellular DNA **," pp. 9168-9172, 2014.

[8] J. A. Prescher and C. R. Bertozzi, "Chemistry in living systems," vol. 1, no. 1, pp. 13-21, 2005.

[9] X. Zhu, J. Liu, and W. Zhang, "De novo biosynthesis of terminal alkyne-labeled natural products.," Nat. Chem. Biol., 11, no. 2, pp. 115-20, February 2015.

[10] R. A. Mehl et al., "Generation of a Bacterium with a 21 Amino Acid Genetic Code," no. 17, pp. 935-939, 2003.

[11] U. T. Bornscheuer, G. W. Huisman, R. J. Kazlauskas, S. Lutz, J. C. Moore, and K. Robins, "Engineering the third wave of biocatalysis.," Nature, 485, no. 7397, pp. 185-94, May 2012.

BRIEF DESCRIPTION OF THE DRAWINGS

FIG. 1. Fermentative production of a wide variety of non-canonical amino acids with useful functional groups FIG. 2. Biosynthetic pathway reconstitution and examples of alternative uses.

FIG. 3A-D. Identification of Bes biosynthetic gene cluster. A) Natural products with terminal alkynes found in nature formed by fatty acid desaturation. B) Terminal alkyne amino acids from *Streptomyces* spp. C) Terminal alkyne production phenotypes of knockouts of each gene in the Bes biosynthetic gene cluster from *S. cattleya*. D) Genes in Bes biosynthetic gene cluster with nearest homologue and putative function.

FIG. 4. Pathways to make halo, alkene, and alkyne amino acids.

DESCRIPTION OF PARTICULAR EMBODIMENTS OF THE INVENTION

Figure 2:
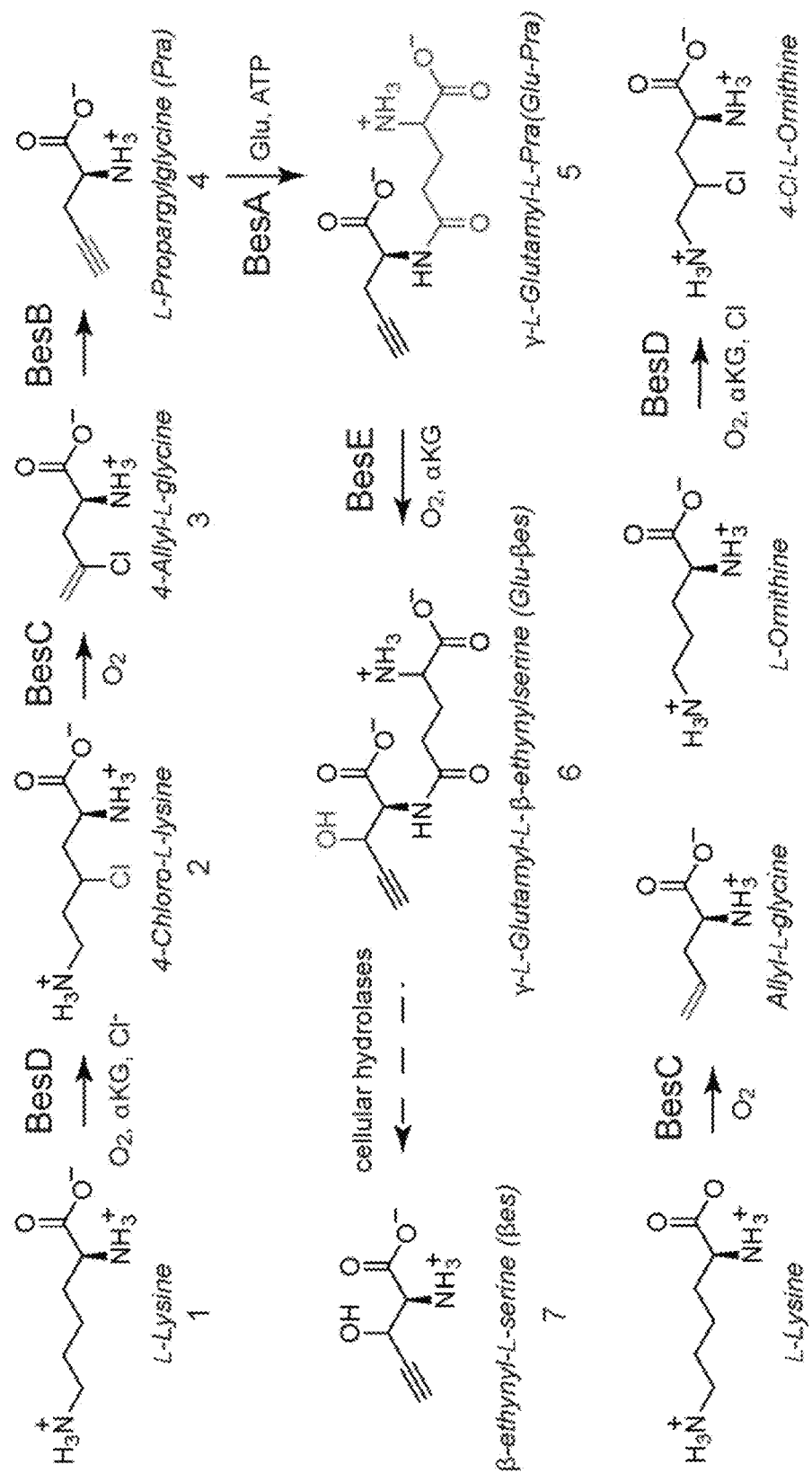

Definitions and relevant descriptions are detailed in WO2012159116, expressly incorporated by reference. Unless contraindicated or noted otherwise, in these descriptions and throughout this specification, the terms "a" and "an" mean one or more, the term "or" means and/or and polypeptide sequences are understood to encompass opposite strands as well as alternative backbones described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

In embodiments the invention is employed to genetically engineer organisms to express enzymes in this pathway for producing non-canonical amino acids for incorporation of these amino acids into proteins, peptides, or non-ribosomal synthetase products. For examples, terminal-alkynes serve as useful handles for performing copper-catalyzed azide-alkyne cycloadditions; terminal-alkenes for inverse-electron demand Diels-Alder, and halogenated compounds for SN2 substitutions. In additional to using these amino acids as handles for performing downstream chemistry, terminal-alkynes, terminal-alkenes, and halogenated compounds can have enhanced therapeutic properties and may be used for biosynthesis of bioactive natural products.

The modularity of this pathway can be leveraged to make a wide assortment of noncanonical amino acids with few parts. Some of these results are experimentally summarized in FIG. 1. For example, expression of BesABCD or BesABCDE can be used to make glutamyl-dipeptide amino acids, Glu-Pra or Glu-Bes respectively, with terminal-alkynes for incorporation of amino acids through pyrrolysine ARS/tRNA pair. Expression of BesABCDE can be used for production of terminal-alkyne amino acid beta-ethynyl-serine, for incorporation of amino acids through host threonylARS/tRNA pair. Expression of only BesC, or an engineered version of this enzyme, can be used for production of allylglycine which contains a terminal-alkene side chain. Expression of BesBCD can be used to make terminal-alkyne amino acid propargylglycine, which can use engineered MetRS/tRNA pair for incorporation into ribosomal products. Expression of BesD can be used for making 4-Cl-lysine or 4-Cl-ornithine, which can be incorporated through lysylARS/tRNA pair.

FIG. 2 shows pathway reconstitution and examples of alternative uses; terminal alkyne amino acid biosynthesis and example shunts for formation of terminal alkene amino acid and chlorinated amino acids.

BES Pathway Enables Production of Labeled Proteins from Common Carbon Source

De Novo Biosynthesis of Non-Canonical Amino Acids is Uniquely Suited for In Vivo Protein Labeling As disclosed and exemplified herein the subject BesA, BesB, BesC, BesD and BesE enzymes can be obtained from naturally occurring sources or synthetically produced. For example, a subject enzyme can be obtained as homologues from a variety of cell types which naturally produce the enzyme or which are genetically modified to express a recombinant gene encoding the enzyme. Accordingly, the disclosure provides for recombinant host cells genetically modified to express the subject enzymes that is compatible for use with the subject tags of a tagged target polypeptide.

The homologues catalyze the same reactions and have conserved sequences at both amino acid and genetic levels. Provided with the extensive amino acid sequence information and characterization of the subject enzymes provided herein as well as in the art, it will be readily apparent to the ordinarily skilled artisan that the subject enzymes include naturally-occurring enzymes as well as modified enzymes sharing sequence identity with Bes enzymes (e.g., a naturally-occurring Bes enzyme) and which retain corresponding catalytic function.

In general, subject enzyme homologues include those having at least 60%, usually 75%, usually 80%, more usually 90%-95% nucleotide or amino acid residue identity, when compared and aligned for maximum correspondence with a nucleotide sequence or amino acid sequence of a parent FGE, as measured using a sequence comparison algorithm available in the art or by visual inspection. Usually a recited sequence identity exists over a region of the sequences that is at least about 50 residues in length, more usually over a region of at least about 100 residues, and more usually over at least about 150 residues up to the full-length of the coding region or protein, with the proviso that the region of comparison includes an active site of the enzyme required for enzymatic activity.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschuel et al. (1977) Nucleic Acids Res. 25: 3389-3402, respectively. Software for performing BLAST analyses is publicly available through the National Center for Biotechnology Information (.ncbi.nlm nihdotgov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold.

These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more usually less than about 0.01, and most usually less than about 0.001.

Residue positions that are not identical may differ by conservative amino acid substitutions, which will be readily apparent from analysis of the alignments as discussed above. Conservative amino acid substitutions refer to the interchangeability of residues having similar side chains. For example, amino acid groups defining residues which can be interchanged for another residue within the group and constitute a conservative amino acid substitution include a group of amino acids having aliphatic side chains is glycine, alanine, valine, leucine, proline, and isoleucine ("aliphatic amino acid"); a group of amino acids having aliphatic-hydroxyl side chains is serine, and threonine ("aliphatic, hydroxylamino acid", which are also encompassed within "polar, uncharged amino acid"); a group of amino acids having amide-containing side chains is asparagine and glutamine ("amide-containing amino acid", which are also encompassed within "polar, uncharged amino acid"); a group of amino acids having aromatic side chains is phenylalanine, tyrosine, and tryptophan ("aromatic amino acid"); a group of amino acids having basic side chains (at physiological pH) is lysine, arginine, and histidine ("basic amino acid"); a group of amino acids having sulfur-containing side chains is cysteine and methionine ("sulfur-containing amino acid"); a group of amino acids that are polar and uncharged (at physiological pH) include serine, threonine, asparagine, and glutamine ("polar, uncharged amino acid"); and a group of amino acids have charged side chains (at physiological pH) is aspartic acid, glutamic acid, histidine, lysine, and arginine ("charged amino acid"). Conservative amino acids substitution groups are exemplified by: valine-leucine-isoleucine, phenylalanine-tyrosine, lysine-arginine, alanine-valine, and asparagine-glutamine.

Cell-free methods typically use isolated enzymes. Any convenient protein purification procedures may be used to isolate a subject enzyme, see, e.g., Guide to Protein Purification, (Deuthser ed.) (Academic Press, 1990). For example, a lysate may be prepared from a cell the produces a desired enzyme, and purified using HPLC, exclusion chromatography, gel electrophoresis, affinity chromatography, and the like.

EXAMPLES

The soil microbe *Streptomyces* cattleya produces a terminal-alkyne amino acid, β-ethynylserine (βes). Here we use this amino acid as an example of a bio-orthogonal handle in protein targets of interest. We present the complete biosynthesis of βes from *Streptomyces* cattleya. Specifically we demonstrate the biosynthetic origin of alkyne and alkene amino acids and characterize a set of enzymes that carry out a series of unusual biochemical transformations. This disclosure enables de novo production of alkyne/alkene labeled proteins, peptides, and non-ribosomal natural products through an expanded genetic code.

Alkyne Natural Products from Fatty Acid Origin.

The biosynthetic origin of terminal-alkyne amino acids has previously been subject of investigation, but efforts thus far have been hampered by the low-occurrence of terminal-alkynes in nature. While acetylenic natural products form a relatively large class of natural compounds, with approximately 2,000 known members, very few of these contain a terminal-alkyne. Early isotope-labeling experiments showed that most these compounds originate from acetate derived fatty acid or polyketide biosynthetic pathways. More recently, the gene clusters for two terminal-alkyne containing natural products, Jamaicamide B and Carmabin A were identified (FIG. 3A). While structurally different, both gene clusters contained a fatty-acid desaturase believed to form the terminal-alkyne in each natural product. Recent work has provided the first in vitro evidence showing that these fatty-acid desaturases form the terminal-alkyne through a diiron/$O_2$-dependent enzyme mechanism. In contrast to fatty acid derived acetylenes, only ten terminal-alkyne-containing amino acids have been described in the literature to date and appear to be structurally quite different from the natural products from a fatty acid origin. In our efforts to uncover how nature makes terminal-alkyne amino acids, we focused on the biosynthesis of βes, isolated from S. cattleya, which is made by a genetically-tractable host.

Knockout of Three Fatty Acid Desaturases in S. Cattleya Did not Produce any βes.

Since known terminal-alkyne natural products arise from fatty acid desaturation, we initially targeted S. cattleya fatty acid desaturases for knockout. Knockout of three fatty acid desaturases in S. cattleya (SCAT_4823, SCAT_p1525, SCAT_0184) did not yield strains capable of βes production. The only putative fatty-acid desaturase in S. cattleya not targeted for knockout, SCAT_2136, is likely related to primary metabolism based on genomic context. These results raised the prospect that the terminal-alkyne from βes was not formed by canonical fatty acid desaturation.

We then shifted our focus to look for other organisms that produce terminal-alkyne amino acids in order to identify shared gene clusters. Towards this goal, we identified two other species of Streptomycetes that had previously been reported to produce structurally similar amino acids. Streptomyces sp. HLR-599A and Streptomyces catenulae had previously been reported in literature to produce propargylglycine (Pra) and α-ethynyl-glycine respectively (FIG. 3B). Since Streptomyces sp. HLR-599A was held in a private collection and no genome sequence has been reported, we pursued investigating secondary metabolism clusters in S. catenulae in hopes of finding a unique conserved set of genes.

Initial Validation of S. catenulae Alkyne Production.

While S. catenulae was previously reported to produce α-ethynyl-glycine, we were unable to detect production of this metabolite through LC-MS. Furthermore, CuAAC derivitization, o-phthaldialdehyde derivitization, or dansyl chloride derivatization also failed to yield evidence of α-ethynyl-glycine. Instead, we observed that S. catenulae was an unreported producer of Pra. Since Pra and βes are structurally similar, we predicted that the production of terminal-alkyne amino acids in Streptomycetes may share similar genetic origins and that comparative analysis of the genomes of these hosts could generate leads for the genes involved in their biosynthesis. Using the two available genome sequences for S. cattleya and S. catenulae, we generated a list of approximately 650 gene clusters, of two or more genes, that are conserved between both species. We then curated this list by removing gene clusters that are more closely related between S. cattleya and 30 other Streptomyces spp. Through this process we narrowed down the number of conserved unique clusters to just four uniquely conserved gene clusters between S. cattleya and S. catenulae and corresponding accession ID. Cluster with members WP_014151494.1, WP_014151495.1, WP_014151496.1, WP_014151497.1 contains a putative carboxylate-amine ligase, putative cystathionine-gamma lyase, putative HemeO superfamily protein, and putative 2-OG/Fe dependent halogenase, respectively.

Recognizing that one of these gene clusters contained proteins associated with amino acid biosynthesis, such as a putative amino acid transporter and putative amino acid hydroxylase, we decided that these set of genes are the most likely candidate. Searching the non-redundant protein database for additional instances of these genes we identified four additional Streptomyces spp. that also possess this gene cluster (S. cattleya, S. catenulae, S. sp. NRRL S-1448, S. achromogenes, S. lavenduligriseus, and S. sp. NRRL S-31), yet had never been reported to produce terminal-alkyne amino acids.

Validation of Other Organisms Producing Alkynes.

Examining the information available through BLAST and the genomic context of these genes, we discovered that the putative βes biosynthetic cluster features four conserved core proteins, BesABCD, found in all clusters and two auxiliary protein, BesE and BesF, found only in S. cattleya and S. sp. NRRL 5-1448 (FIG. 3D). BesA possesses a highly conserved ATP-grasp domain and shares homology to carboxylate-amine ligases. BesB is homologous to the PLP-dependent cystathionine-γ-lyase/O-succinylhomoserine-β-synthase family BesC displays a low level of homology, ~30% similarity, to enzymes in the HemeO superfamily and is a putative non-heme, iron dependent oxidase. Both BesD and BesE are predicted to be non-heme Fe/α-ketoglutarate (α-KG)-dependent oxidases. Finally BesF is a putative EamA-like transporter, with homologues of this protein implicated in amino acid efflux.

Culturing the four newly identified Streptomyces validated the idea that we had identified the correct gene cluster Amino acid analysis with high resolution LC-MS was used to determine that Streptomyces sp. NRRL 5-31 and Streptomyces achromogenes were producers of Pra, Streptomyces sp. NRRL 5-1448 produced both Pra and βes, while no alkyne amino acid was detected in Streptomyces levenduligriseus. Based on these results and the comparison of the conserved genes in each cluster, we proposed that BesABCD are required for Pra biosynthesis while BesE and BesF are the auxiliary proteins and are related to βes biosynthesis.

Knockouts of Bes ABCDE and Initial Production.

To better understand what types of the biosynthetic precursors and intermediates are involved in Pra and βes biosynthesis, we knocked out individual genes in S. cattleya to generate knockout strains S. cattleya ΔbesA, ΔbesB, ΔbesC, ΔbesD, and ΔbesE Amino acid analysis of these knockouts showed that the ΔbesB, ΔbesC, and ΔbesD strains did not produce detectable amounts of Pra or βes (FIG. 3C). In comparison, the ΔbesA strain showed lowered yields of both products, while the ΔbesE strain still produced Pra but not βes. These results implicate ΔbesB, ΔbesC, and ΔbesD as critical to Pra formation, while also indicating ΔbesE is the putative hydroxylase that converts Pra to βes.

Comparative Metabolomics.

We then performed untargeted comparative metabolomics to identify the remaining pathway intermediates. Extracts of intracellular metabolites for S. cattleya wildtype, ΔbesA, ΔbesB, ΔbesC, ΔbesD, and ΔbesE were analyzed by LC-MS. The resulting mass spectra were then processed using XCMS (Scripps) for feature detection. The molecules that accumulated or existed exclusively in the extract of certain knockout strain indicate that this specific molecule serves as the substrate for the enzyme. From an initial set of lead compounds with high statistical significance ($p<0.05$) and high fold change ($>2$) between wildtype and knockout, approximately 1000 metabolites were identified. By focusing on the metabolites that accounted for the highest degree of variance, we were able to identify a set of putative intermediates and precursors for βes biosynthesis L-lysine is the biosynthetic pathway precursor of βes (FIG. 2). The pathway begins with chlorination of L-lysine by putative α-KG/Fe halogenase BesD at the $C_\gamma$ position. The resulting amino acid, 4-Cl-L-lysine is then oxidized by BesC to form 4-Cl-allylglycine. This compound, a $C_{\gamma,\delta}$ alkenyl-halide, then undergoes elimination of Cl- by PLP-dependent enzyme BesB to yield terminal-alkyne amino acid Pra. Based on production titers from comparative metabolomics, we propose that Pra must then be ligated to glutamate by BesA to form a glutamyl-dipeptide. The glutamyl-dipeptide serves as the substrate for BesE, a α-KG/Fe dependent amino acid hydroxylase. The absence of any other conserved gene in these clusters indicates βes-Glu as the true final product of the pathway, and a peptidyl-transglutaminase or protease may release of free Pra and βes into the extracellular environment.

BesD is a α-KG/Fe Dependent L-Lysine Chlorinase.

To reconstitute the biosynthetic pathway in vitro, we proceeded to characterize and study each individual enzyme of the βes pathway. Initially, bioinformatics was used to inform on the necessary cofactors that might be required for activity. By amino acid sequence BesD resembles the family of iron and alpha-ketoglutarate dependent halogenases. It contains the characteristic HXG motif required for halide coordination to the active site iron rather than the HXD/E motif of the related family of hydroxylases. Previously studies and structural characterization of enzymes SyrB2 and WelO5 showed that HXG/A was required to provide a site for Cl-binding. This stands in contrast to BesE which was found to have the conserved α-KG/Fe hydroxylase HXD motif.

When L-lysine was incubated with BesD, we found the major product of the reaction had a characteristic Cl isotopic pattern. Through NMR and comparison to a synthetic standard, we determined the position of chlorination to be at the $C_\gamma$, thus assigning this compound as 4-Cl-lysine. The formation of 4-Cl-lysine was dependent on both Fe and α-KG, which is consistent with its assignment as an α-KG/Fe dependent halogenase. Furthermore, mutation of the active site glycine to aspartate, BesD G138D, abolished halogenation while maintaining a small amount of detectable hydroxylation. Due to the inherent instability of 4-Cl-lysine, the resulting lactone, lactam and 4-OH-lysine shunt products were observed and characterized.

Although chlorination of small molecules is a desirable chemical transformation, methods for achieving regio- and stereo-specific halogenation, particularly at aliphatic carbon centers, are limited. Nature has evolved a class of α-KG/Fe dependent halogenases to perform this chemistry, most of which either require tethering of substrate to a carrier protein, such as in SyrB2, or act on larger, complex substrates, such as in WelO5. BesD, the lysine halogenase in the βes biosynthesis pathway, is the first described small molecule α-KG/Fe halogenase to act directly on a proteogenic amino acid.

BesC Catalyzes the Formation of 4-Cl-Allygllycine.

The only other halogenated metabolite we identified from comparative metabolomics had a mass consistent with a loss of —CH7N from Cl-L-lysine. This compound accumulated in ΔbesB and was not observed in ΔbesC, suggesting BesC is the most likely candidate for its production. BesC catalyzes an unusual C-C bond cleaving reaction on the substrate 4-Cl-lysine to form a $C_5$ terminal-alkene with concomitant release of ammonia and formaldehyde. Like 4-Cl-lysine, 4-Cl-allylglycine also exhibited a characteristic isotopic pattern consistent with chlorination. The position of chlorination was confirmed by comparison to a synthetic standard through LC/MS.

Bioinformatically, BesC has homology to other di-nuclear Fe enzymes, such as the *Chlamydia* protein Associated with Death Domains (CADD, 25%) and Stearoyl ACP desaturase (20%). An overlay of the predicted homology model of βesC, with the solved crystal structure of CADD reveals six conserved putative Fe binding residues in the active site.

To further characterize BesC, we then tested the ability of BesC to produce 4-Cl-allygllycine in vitro. Addition of Fe(II) to purified apo-enzyme supports the observed reaction, while omission of Fe(II) results in no reaction, supporting the Fe-dependence of the enzyme. In coupled reactions with BesC, BesD, the necessary cofactors, and lysine, we determined that BesC accepts lysine as a substrate directly to form allylglycine.

Next, we investigated the overall reaction stoichiometry. To detect the putative ammonia co-product, we employed a coupled assay in which glutamate dehydrogenase converts ammonia and α-KG to glutamate and water with concurrent oxidation of NADPH. The release of ammonia from 4-Cl-lysine was monitored indirectly, through change in NADH absorbance at 340 nm, as well as directly, through incorporation of the nitrogen from $^{15}$N-labeled lysine substrate into glutamate. The ε-carbon atom is lost from 4-Cl-lysine as formaldehyde. Enzymatic reactions were also performed in the presence of Fluoral-P to derivitize formaldehyde upon release from the substrate. The resulting product was quantified by fluorescence and compared to alkene product formation, quantified by LC/MS. Taken together, the data indicate that BesC catalyzes alkene formation with stoichiometric release of formaldehyde and ammonia.

BesB is an Acetylenase.

We next turned our attention to formation of the terminal-alkyne. BesB belongs to a family of proteins that utilize pyrodoxyal-5'-phosphate (PLP) as cofactor. Incubating purified BesD, BesC, and BesB in the presence of iron, ascorbate, lysine, and PLP was sufficient to produce Pra in vitro. This order of events is similar to how terminal-alkynes are synthesized chemically, since biosynthesis of Pra involves elimination of an alkyl-halide to a terminal-alkyne. Terminal desaturations have previously only been observed on fatty acids and catalyzed by $O_2$/di-iron dependent fatty acid desaturases. In comparison, the Pra terminal-alkyne is formed by a PLP-dependent mechanism and does not appear to require iron or oxygen. From in vitro characterization, we also found it was necessary for the amino acid substrate to be halogenated at the $C_\gamma$ position. BesB is able to form Pra with either 4-Cl-allylglycine or 4-Br-allylglycine as substrates, but not when allylglycine is a substrate.

Explanation of Initial Reaction from 4-Cl-Allylglycine.

As an initial probe for the mechanism of alkyne formation, we used high-resolution mass spectroscopy to measure deuterium exchange along the backbone of the substrate. Using 4-Cl-allylglycine as a substrate resulted in formation of $[M+2D]^+$ Pra. To explain the observed pattern of deuterium exchange, we disclose a mechanism consistent with a canonical cystathionine β-lyase/cystathionine γ-synthase PLP mechanism whereby $C_\alpha$ deprotonation leads to formation of a 4-Cl-allylglycine-quinonoid intermediate. The key step then involves deprotonation at $C_\beta$ with concomitant elimination of Cl- to form an allene-quinonoid intermediate, which subsequently isomerizes to a terminal-alkyne before being released from PLP.

BesA Forms a Dipeptide.

Knockout strain of putative amino acid hydroxylase, BesE, was only capable of producing Pra. However, when BesE was incubated with Pra in the presence of ascorbate and α-KG, no reaction was observed. This lead us to believe that there might be an amino acid carrier that serves as the true substrate for BesE. Through comparative metabolomics, we were able to identify a metabolite enriched in *S. cattleya* ΔbesE over wildtype. This compound was also present, but at low concentration, in *S. cattleya* ΔbesA. We identified this compound as having mass consistent with a Pra-Glu dipeptide. When this compound was fragmented we were able to detect characteristic fragments consistent with an amide bond cleavage, supporting evidence that this compound is a Pra-Glu dipeptide.

We were able to reconstitute activity of BesA in vitro by incubating Pra, glutamate, and ATP. Unlike γ-glutamyltransferases, which forms dipeptides through a reversible mechanism, BesA forms dipeptide from two free amino acids and uses the hydrolysis of ATP to drive the reaction forward. We then explored the specifity of BesA by reacting glutamate with norvaline, allylglycine, and the remaining 19 canonical amino acids. Pra and Cys were the only two amino acids to show any measurable activity. While observed $k_{cat}$ were comparable between using Pra and Cys as substrates, the $K_m$ for Pra was 10 fold lower than for Cys. That cysteine is taken as a substrate at all may result from favorable evolutionary pressure to produce γ-glutamyl-cysteine, a crucial precursor to glutathione biosynthesis.

BesE is an Amino Acid Hydroxylase.

The last dedicated enzyme involved in the biosynthesis of βes is BesE. Once we had identified Pra-Glu as the product of BesA, it became apparent that the true substrate of BesE is a Pra-Glu dipeptide. *S. cattleya* ΔbesB, ΔbesC, ΔbesD, and ΔbesE were unable to produce measurable amounts of the dipeptides in vivo. In comparison, ΔbesA was still able to produce βes-Glu but at lower titers when compared to *S. cattleya* wildtype. Surely enough, BesA was able to hydroxylate Glu-Pra dipeptide, consistent with BesA being a α-KG/Fe dependent hydroxylase.

In all *Streptomyces* spp. explored to possess the Pra/βes biosynthetic gene cluster, only the free amino acids, and not the glutamyl-dipeptide, are observed being secreted into the culture medium. Exploring the genetic context of this gene cluster fails to reveal a conserved peptidase or lyase that might be able to convert βes-Glu dipeptide into their corresponding free amino acids. There are, however, other enzymes found in primary metabolism that are capable of hydrolysing the dipeptides. Supporting this idea, we have shown that enzymes such as γ-glutamyl-transpeptidase from equine kidney can catalyze both the ligation of Pra onto glutamate and the hydrolysis of βes from βes-Glu dipeptide.

BesA is conserved among all observed Pra biosynthetic gene clusters, even in the absence of the dedicated Pra-Glu hydroxylase, BesE. This raises the possibility that Glu-Pra serves a physiological function outside of being a substrate for hydroxylation. One possibility is that forming the dipeptide is used as a form of resistance. Pra has previously been identified as a mechanistic, suicide inhibitor of a variety of PLP proteins including cystathionine-γ-lyase. Another possibility is that Pra-Glu is exported more efficiently through dedicated amino acid transporters.

Regarding Activity of BesD:

Activity of BesD from *S. cattleya* on L-lysine was first screened using an enzyme-coupled assay that reports on succinate production. We found that rate of NADH production was greatest in the presence of L-lysine. Interestingly, similar amount of activity was found when ornithine was used a substrate. However other structurally similar amino acids, such as arginine and norvaline, showed no activity.

BesB Mechanism:

In order to further probe the mechanism behind alkyne formation, we performed enzymatic reactions in vitro using deuterated substrates. One possible mechanism for terminal-alkyne formation is via a 3,5-hydride shift from an allene. If a hydride shift occurs, we should be able to observe proton-deuterium exchange between the $C_\beta$ and $C_\delta$ positions. To make a differentially labeled substrate, we used [4,4,5,5-$D_4$]-L-Lysine and BesC|D to make [4,5,5-$D_3$]-4-Cl-allylglycine. When this species is used as a substrate for BesB, only $[M+D]^+$ Pra species is observed as opposed to the expected $[M+2D]^+$ if a hydride shift were occurring.

Observing only $[M+D]^+$ Pra lead us to hypothesize that isomerization occurs through an acid-base catalyzed mechanism. If this were the case, we can run the reaction in reverse and should expect to see Pra exchange with deuterated solvent at the $C_\beta$ and $C_\delta$ position. When Pra is used as a substrate in deuterated solvent, we observed exchange at three positions. We used highfield NMR to assign these positions as the $C_\alpha$, $C_\beta$, and $C_\delta$. This observation is consistent with an acid-base catalyzed isomerization. Only one $H_\beta$ was observed to exchange, indicating that the enzyme has stereochemical preference for which proton to abstract.

α-Allenyl-Glycine is not a Substrate for BesB.

While formation of allene-quinonoid can be mechanistically explained, there is no precedence of an enzyme catalyzed allene-alkyne isomerization. One possibility is that BesB forms α-allenyl-glycine enzymatically and isomerization occurs after α-allenyl-glycine is released from PLP. Incubating a synthetic standard of allenlylglycine in buffered solution for 24 h at room temperature did not produce detectable amounts of Pra. When α-allenyl-glycine is incubated in $D_2O$, we found it produced negligible exchange with solvent. These results rule out the possibility of spontaneous isomerization of the free amino acid. Another possibility is BesB produces and releases α-allenyl-glycine, and is subsequently enzymatically isomerized. However, no isomerization and neglible $D_2O$ exchange was observed when α-allenyl-glycine was incubated in the presence of BesB in $D_2O$, suggesting that BesB is incapable of isomerizing free allenlyl-glycine. Finally, we explored the possibility of α-allenyl-glycine binding to BesB as a PLP-conjugate by chemically reducing the whole complex with imine-reducing reagents. We were unable to observe any α-allenyl-glycine-PLP species, which suggest α-allenyl-glycine is unable to bind BesB. Using this same technique, we were however able to observe Pra as a PLP bound species through chemical trapping when either 4-Cl-allylglycine or Pra is used as a substrate. Together, these results indicate that isomerization to the terminal-alkyne occurs through a PLP-enzyme mediated intermediate and not spontaneously as a free amino acid.

Dipeptide Characterization:

BesA shares homology to carboxylate-amine ligases, which form amides between amines and carboxylates through an ATP-dependent mechanism. We were able to reconstitute activity of BesA in vitro by incubating Pra, glutamate, and ATP. The product formed from this reaction matched the retention time and fragmentation pattern from the in vivo product. Since we observed low amounts of production of Glu-Pra dipeptide in the BesA knockout, we reasoned that the dipeptide that forms can likely form through other means. Using γ-Glu-α-Pra synthesized by commercial γ-glutamyl-transferase yielded a species identical to that of the one observed. This evidence indicated that the dipeptide product of BesA is γ-Glu-α-Pra. The observed dipeptide was not limited to S. cattleya, as we were also able to observe the same dipeptide being formed when feeding Pra to E. coli DH10B.

Resolving a Long-Standing Mystery Regarding a Class of Non-Proteogenic Amino Acids:

Within the context of unusual natural products, elucidation of βes biosynthesis has resolved a long-standing mystery regarding the biosynthesis of these structurally similar amino acids. Bes from *Sclerotium rolfsii* and *S. cattleya*; Pra from *Amanita pseudoporphyria* and *Streptomyces* sp. HLLR 599A; allylglycine observed in *Amanita pseudoporphyria*; and 4-Cl-allylglycine observed in *Amanita pseudoporphyria* arise from the same biosynthetic pathway.

Characterization of Cyclic Derivative of 4-Cl-Lysine.

While 4-Cl-lysine is the direct product of this reaction, inherent instability of this molecule lead to the formation of a number of side products. These products are thought to all arise from an initial intramolecular cyclization nucleophilic attack at the C-4 position which forms the 5-membered lactone. Similar intramolecular cyclizations have previously been observed from in other Cγ chlorinated amino acids such as 4-Cl-threonine, 4-Cl-isoleucine, and 4-Cl-leucine. A nucleophilic rearrangement of the lactone leads to the formation of a more stable 7-membered lactam, which can hydrolyze to form a 4-OH-lysine. We estimate that the in vitro half-life of 4-Cl-lysine is on the order of 30 m-1 h.

CONCLUSION

Following individual characterization of enzymes in βes biosynthesis pathway, we are now able to fully reconstitute βes biosynthesis in vitro. This pathway reveals an unconventional mechanism for formation of terminal-alkyne that more closely resembles the strategy of a synthetic chemist over that of nature. Due to the modular nature of this pathway, these genes can be repurposed for expanding the genetic code to include chemically diverse amino acids, with functionally useful side chains.

FIG. 4 provides examples of pathways to make halo, alkene, and alkyne amino acids.

Additional, exemplary halogenation products include:

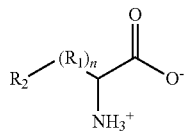

wherein $R_1$ is an optionally halogenated, optionally methylated methylene bridge (e.g. $CH_2$, CHCl, $CCl_2$, $CHCH_3$, $CClCH_3$, etc.), n is 1, 2 or 3, and $R_2$ is optionally halogenated methyl (e.g. $CH_3$, $CH_2Cl$, $CHCl_2$, etc.) or polar groups like $NH_3$, OH, COOH, SH, $CH_3ON$ (amide), and $CH_6N_3$ (guanidine).

Halogenase can be used with diverse substrates, such as:

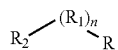

wherein R is carboxyl, amine or glycyl, $R_1$ is an optionally halogenated, optionally methylated methylene bridge (e.g. $CH_2$, CHCl, $CCl_2$, $CHCH_3$, $CClCH_3$, etc.), n is 1, 2 or 3, and $R_2$ is optionally halogenated, sulfonylated, or aminated methyl (e.g. $CH_3$, $CH_2Cl$, $CHCl_2$, etc.) or polar groups like $NH_3$, OH, COOH, SH, $CH_3ON$ (amide), and $CH_6N_3$ (guanidine).

We also demonstrated in vivo production for genes in this pathway in heterologous hosts, including production of halo, alkene, and alkyne amino acids in heterologous host, *E. coli*, usage of protein homologues to increase production in *E. coli*, and usage of lower pH media (preferably about 5 or 6 to about 7) for improve production of halo, halo-alkene, and alkyne amino acids. In particular results for Cl-Allylglycine production optimization we found media with lower pH is preferred for efficient production of Cl-lysine and therefore, Cl-allyglycine. High expression homologues of BesC and BesD from *Pseudomonas fluorescens* and other genera were also demonstrated, and we demonstrated that BesC (and homologues) can make allylglycine from lysine without any changes to media conditions.

Proteins: Organism: *Streptomyces* cattleya
BesF: CCB72068.1 Integral membrane protein DUF6 (plasmid) [*Streptomyces* cattleya NRRL 8057=DSM 46488]
BesA: CCB72069.1 conserved protein of unknown function (plasmid) [*Streptomyces* cattleya NRRL 8057=DSM 46488]
BesB: CCB72070.1 putative Cys/Met metabolism pyridoxal-phosphate-dependent protein (plasmid) [*Streptomyces* cattleya NRRL 8057=DSM 46488]
BesC: CCB72071.1 protein of unknown function (plasmid) [*Streptomyces* cattleya NRRL 8057=DSM 46488]
BesD: CCB72072.1 ArpA protein (plasmid) [*Streptomyces* cattleya NRRL 8057=DSM 46488]
BesE: CCB72073.1 conserved protein of unknown function (plasmid) [*Streptomyces* cattleya NRRL 8057=DSM 46488]
  Organism: *Streptomyces catenulae*
BesA: WP_030285995.1 hypothetical protein [*Streptomyces catenulae*]
BesB: WP_030285993.1 hypothetical protein [*Streptomyces catenulae*]
BesC: WP_030285991.1 hypothetical protein [*Streptomyces catenulae*]
BesD: WP_030285989.1 hypothetical protein [*Streptomyces catenulae*]
  Organism: *Streptomyces* sp. NRRL S-31
BesA: WP_030744375.1 hypothetical protein [*Streptomyces* sp. NRRL S-31]
BesB: WP_030744376.1 Cys/Met metabolism pyridoxal-phosphate-dependent protein [*Streptomyces* sp. NRRL S-31]
BesC: WP_030744378.1 hypothetical protein [*Streptomyces* sp. NRRL S-31]
BesD: WP_030744380.1 hypothetical protein [*Streptomyces* sp. NRRL S-31]
  Organism: *Streptomyces* sp. NRRL S-1448
BesF: WP_078865820.1 EamA family transporter [*Streptomyces* sp. NRRL S-1448]
BesA: WP_030410682.1 hypothetical protein [*Streptomyces* sp. NRRL S-1448]
BesB: WP_030410683.1 hypothetical protein [*Streptomyces* sp. NRRL S-1448]
BesC: WP_030410684.1 hypothetical protein [*Streptomyces* sp. NRRL S-1448]
BesD: WP_030410685.1 hypothetical protein [*Streptomyces* sp. NRRL S-1448]
BesE: WP_030410686.1 proline hydroxylase [*Streptomyces* sp. NRRL S-1448]
  Organism: *Streptomyces achromogenes*
BesA: WP_030612442.1 hypothetical protein [*Streptomyces achromogenes*]

BesB: WP_078844341.1 Cys/Met metabolism pyridoxal-phosphate-dependent protein [*Streptomyces achromogenes*]
BesC: WP_030612452.1 hypothetical protein [*Streptomyces achromogenes*]
BesD: WP_030612455.1 hypothetical protein [*Streptomyces achromogenes*]

Organism: *Streptomyces lavenduligriseus*
BesA:WP_037703010.1 hypothetical protein [*Streptomyces lavenduligriseus*]
BesB: WP_078637771.1 Cys/Met metabolism pyridoxal-phosphate-dependent protein [*Streptomyces lavenduligriseus*]
BesC: WP_030791984.1 hypothetical protein [*Streptomyces lavenduligriseus*]
BesD:WP_030791981.1 hypothetical Examples of BesD homologues with varying substrate/product scope
BesD: WP_016975823 [*Pseudomonas fluorescens*]
BesD: WP_057723975 [*Pseudomonas orientalis*]
BesD: WP_019233318 [*Legionella anisa*]
BesD: WP_019363259 [*Pseudomonas fuscovaginae*]
BesD: WP_071496957 [*Pseudomonas azotoformans*]
BesD: WP_059666251 [*Burkholderia cepacia*]
BesD: WP_081062281 [*Burkholderia cepacia*]
BesD: WP_069786233 [*Pseudomonas salomonii*]
BesD: WP_020275004 [*Streptomyces afghaniensis*]
BesD: SDN46247 [*Streptomyces wuyuanensis*]
BesD: WP_057008702 [*Pseudomonas trivialis*]
BesD: WP_046063366 [*Pseudomonas kilonensis*]
BesD: WP_036209184 [*Marinobacter* sp. MCTG268]
BesD: WP_056854138 [*Pseudomonas* sp. Root562]
BesD: WP_028687259 [*Pseudomonas fulva*]
BesD: WP_012051265 [*Pseudomonas putida*]
BesD: WP_003392791 [*Pseudomonas syringae*]

The invention claimed is:

1. A method of synthesizing a halogenated amino acid, the method comprising contacting a recombinant BesD α-ketoglutarate/Fe-dependent halogenase enzyme with a predetermined amino acid substrate under conditions wherein enzyme halogenates the substrate to produce a halogenated amino acid product, wherein the substrate is lysine or ornithine and the product is 4-Cl-lysine or 4-Cl-ornithine, respectively, and the contacting step occurs in a cell-free system or in a host cell, heterologous to the enzyme, wherein the cell is genetically engineered to express the enzyme.

2. The method of claim 1, wherein the contacting step occurs in a cell-free system.

3. The method of claim 1, wherein the contacting step occurs in a host cell, heterologous to the enzyme, wherein the cell is genetically engineered to express the enzyme.

4. The method of claim 1, wherein the contacting step occurs in a host cell, heterologous to the enzyme, wherein the cell is genetically engineered to express the enzyme, and the halogenated amino acid product is incorporated into a protein in the cell.

5. The method of claim 1, wherein the substrate is lysine and the product is 4-Cl-lysine.

6. The method of claim 2, wherein the substrate is lysine and the product is 4-Cl-lysine.

7. The method of claim 3, wherein the substrate is lysine and the product is 4-Cl-lysine.

8. The method of claim 4, wherein the substrate is lysine and the product is 4-Cl-lysine.

9. The method of claim 1, further comprising detecting the product.

10. The method of claim 1, wherein the enzyme is native to a genus:
*Streptomyces, Pseudomonas Legionella, Burkholderia* or *Marinobacter.*

11. The method of claim 2, wherein the enzyme is native to a genus:
*Streptomyces, Pseudomonas Legionella, Burkholderia* or *Marinobacter.*

12. The method of claim 3, wherein the enzyme is native to a genus:
*Streptomyces, Pseudomonas Legionella, Burkholderia* or *Marinobacter.*

13. The method of claim 4, wherein the enzyme is native to a genus:
*Streptomyces, Pseudomonas Legionella, Burkholderia* or *Marinobacter.*

14. The method of claim 5, wherein the enzyme is native to a genus:
*Streptomyces, Pseudomonas Legionella, Burkholderia* or *Marinobacter.*

15. The method of claim 1, wherein the enzyme is native to a species:
*Streptomyces* cattleya, *Streptomyces catenulae, Streptomyces* sp. NRRL S-31, *Streptomyces* sp. NRRL S-1448, *Streptomyces achromogenes, Streptomyces lavenduligriseus, Pseudomonas fluorescens, Pseudomonas orientalis, Legionella anisa, Pseudomonas fuscovaginae, Pseudomonas azotoformans, Burkholderia cepacia, Pseudomonas salomonii, Streptomyces afghaniensis, Streptomyces* wuyuanensis, *Pseudomonas trivialis, Pseudomonas kilonensis, Marinobacter* sp., *Pseudomonas* sp. Root562, *Pseudomonas fulva, Pseudomonas putida* or *Pseudomonas syringae.*

16. The method of claim 2, wherein the enzyme is native to a species:
*Streptomyces* cattleya, *Streptomyces catenulae, Streptomyces* sp. NRRL S-31, *Streptomyces* sp. NRRL S-1448, *Streptomyces achromogenes, Streptomyces lavenduligriseus, Pseudomonas fluorescens, Pseudomonas orientalis, Legionella anisa, Pseudomonas fuscovaginae, Pseudomonas azotoformans, Burkholderia cepacia, Pseudomonas salomonii, Streptomyces afghaniensis, Streptomyces* wuyuanensis, *Pseudomonas trivialis, Pseudomonas kilonensis, Marinobacter* sp., *Pseudomonas* sp. Root562, *Pseudomonas fulva, Pseudomonas putida* or *Pseudomonas syringae.*

17. The method of claim 3, wherein the enzyme is native to a species:
*Streptomyces* cattleya, *Streptomyces catenulae, Streptomyces* sp. NRRL S-31, *Streptomyces* sp. NRRL S-1448, *Streptomyces achromogenes, Streptomyces lavenduligriseus, Pseudomonas fluorescens, Pseudomonas orientalis, Legionella anisa, Pseudomonas fuscovaginae, Pseudomonas azotoformans, Burkholderia cepacia, Pseudomonas salomonii, Streptomyces afghaniensis, Streptomyces* wuyuanensis, *Pseudomonas trivialis, Pseudomonas kilonensis, Marinobacter* sp., *Pseudomonas* sp. Root562, *Pseudomonas fulva, Pseudomonas putida* or *Pseudomonas syringae.*

18. The method of claim 4, wherein the enzyme is native to a species:
*Streptomyces* cattleya, *Streptomyces catenulae, Streptomyces* sp. NRRL S-31, *Streptomyces* sp. NRRL S-1448, *Streptomyces achromogenes, Streptomyces lavenduligriseus, Pseudomonas fluorescens, Pseudomonas orientalis, Legionella anisa, Pseudomonas fuscovaginae, Pseudomonas azotoformans, Burkholderia cepacia, Pseudomonas salomonii, Streptomyces afghaniensis, Streptomyces* wuyuanensis, *Pseudomonas trivialis,*

*Pseudomonas kilonensis*, *Marinobacter* sp., *Pseudomonas* sp. Root562, *Pseudomonas fulva*, *Pseudomonas putida* or *Pseudomonas syringae*.

19. The method of claim 5, wherein the enzyme is native to a species:

*Streptomyces* cattleya, *Streptomyces catenulae*, *Streptomyces* sp. NRRL S-31, *Streptomyces* sp. NRRL S-1448, *Streptomyces achromogenes*, *Streptomyces lavenduligriseus*, *Pseudomonas fluorescens*, *Pseudomonas orientalis*, *Legionella anisa*, *Pseudomonas fuscovaginae*, *Pseudomonas azotoformans*, *Burkholderia cepacia*, *Pseudomonas salomonii*, *Streptomyces afghaniensis*, *Streptomyces* wuyuanensis, *Pseudomonas trivialis*, *Pseudomonas kilonensis*, *Marinobacter* sp., *Pseudomonas* sp. Root562, *Pseudomonas fulva*, *Pseudomonas putida* or *Pseudomonas syringae*.

20. The method of claim 1, wherein the enzyme is native to species:

*Streptomyces* cattleya.

\* \* \* \* \*